United States Patent [19]

Dunbar et al.

[11] Patent Number: 4,780,408

[45] Date of Patent: Oct. 25, 1988

[54] ANTIBODY FOR DETECTION AND QUANTIFICATION OF TRIFLURALIN

[75] Inventors: Bohn D. Dunbar, Akron; Gordon D. Niswender; James M. Hudson, both of Fort Collins, all of Colo.

[73] Assignee: Colorado State University Research Foundation, Fort Collins, Colo.

[21] Appl. No.: 844,338

[22] Filed: Mar. 26, 1986

[51] Int. Cl.[4] .................. G01N 33/53; G01N 33/549; C07K 15/14

[52] U.S. Cl. ...................................... 435/7; 424/85.8; 436/532; 436/547; 436/815; 436/819; 530/363; 530/367; 530/387; 530/405; 530/806; 530/807

[58] Field of Search ............. 424/85; 436/536, 542, 436/815, 532, 547, 819; 530/387, 363, 367, 405, 806, 807; 435/188, 7

[56] References Cited

U.S. PATENT DOCUMENTS

| | | | |
|---|---|---|---|
| 3,852,157 | 12/1974 | Rubenstein et al. | 435/7 |
| 4,275,160 | 6/1981 | Singh et al. | 435/188 |
| 4,530,786 | 7/1985 | Dunbar et al. | 260/112 B |

OTHER PUBLICATIONS

Chemical Abstracts, vol. 77, 1972, Abstract No. 71229g, Lavy et al.

Chemical Abstracts, vol 99, 1983, Abstract No. 117692n, Helmuth et al.

Chemical Abstracts, vol. 98, 1983, Abstract No. 174431e, Benigni et al.

*Primary Examiner*—Robert J. Warden
*Assistant Examiner*—Florina B. Hoffer
*Attorney, Agent, or Firm*—Dorr, Carson, Sloan & Peterson

[57] ABSTRACT

An antibody specific to trifluralin can be produced by first substituting a soluble, straight chain amino acid for a propyl group of $\alpha,\alpha$, $\alpha$-trifluoro-2,6-dinitro-N-N-dipropyl-p-toluidine. The trifluoro group at the 4 position, the nitro group at the 2 position and the other nitro group at the 6 position are left exposed. Thereafter, the resulting substitution product is conjugated, at the site of the substituted amino acid group, with a lysine-rich protein. The resulting compound is then used as an antigen to evoke an immune response in a host animal or antibody producing cell line. The antibody produced against the antigen is then harvested and used in an assay such as a radioimmunoassay or enzyme linked immunosorbant assay (ELISA) to determine the presence and concentrations of trifluralin in agriculturally significant substances such as plant materials, soil and water or to otherwise test for trifluralin contamination of water, food and air.

12 Claims, No Drawings

ANTIBODY FOR DETECTION AND QUANTIFICATION OF TRIFLURALIN

BACKGROUND OF THE INVENTION

1. Field of the Invention

This invention relates to the detection and quantification of small quantities of man-made chemicals such as herbicides, insecticides and fertilizers in soil, water and plant samples. This invention also relates to the design of antigens capable of eliciting immune responses which in turn are capable of producing antibodies specific to particular substances.

2. Description of the Prior Art

Trifluralin, a member of the dinitro analin family, is a well known and widely used herbicide. It is particularly effective against Kochia and pigweeds. Unfortunately, residues of trifluralin can persist in soils for many months after its use as a herbicide. These residues can kill or seriously injure subsequently planted crops. Winter wheat is particularly susceptible. Hence, farmers are particularly concerned with determining the presence and concentration of trifluralin residues in their soils, particularly in the period just prior to planting.

The most commonly used techniques for making these determinations have a number of drawbacks. For example, those bioassay procedures which can be employed right on the farm can only detect those upper range of trifluralin levels which are known to injure specific crops such as for example winter wheat. Moreover, the farmer needs a great deal of skill, time and discipline to carry out these bioassays in a manner which is likely to produce reliable results. Oat seeds must be planted in pots and maintained under carefully controlled conditions for at least twenty days. After seed germination, each pot is thinned to about three plants of uniform size. These plants are then uprooted and washed clean of any soil and weighted to a high degree of accuracy. The resulting weights are analyzed statistically to provide a linear representation of trifluralin residue in the samples.

Aside from the weighing and statistical skills required for accurate results, these bioassays are hampered by the fact that their limit of sensitivity is about 0.10 lbs/acre. Unfortunately, trifluralin concentrations lower than 0.10 lbs/acre are known to be harmful to certain crops, particularly winter wheat. Hence bioassays, if done accurately, can only warn the farmer that trifluralin concentrations are too high. They can not however, tell whether the concentrations are far enough below 0.10 lbs/acre to assure a safe planting.

Alternatively, farmers can send soil samples to commercial laboratories. These commercial laboratories may carry out bioassays in a more rigorous fashion than the farmer or they may use more sophisticated techniques such as gas chromatography or high pressure liquid chromatograph. However, this course of action is both expensive and time consuming since many of the laboratory techniques are complex. For example, the U.S. Environmental Protection Agency recently proposed a complex series of methods for analyzing pesticide pollutants. These procedures include many industry and contractor-developed analyses, and several analyses developed by the EPA's own Environmental Monitoring Support Laboratory. One of these methods uses gas chromatography for purification of the sample. The residue is detected by using an electron capture ($^{63}$Ni) detector. Detection limits for trifluralin range from $10^{-13}$ to $10^{-12}$ g. However, accuracy and precision studies suggest that samples normally contain these compounds in parts per billion, i.e., levels $10^{-3}$ to $10^{-5}$ times higher than the detection limit. In this range, high pressure liquid chromatogrphy coupled with ultra-violet detection is an alternative to the gas chromatography analysis which has, in the past, been the accepted standard for trifluralin analysis. In any case, accuracy and expense are important factors that should be considered when these techniques are used since both require a great deal of purification before the sample can be quantitated. Organic material must be removed and, in some cases, several solvent systems with a complex reflux apparatus are needed. However, the overall results realizable using these techniques can provide a very accurate determination (sensitive to the low parts per billion) of the residual herbicide in the soil sample. Again, however, the cost of the equipment, materials, and labor needed to carry out these tests are considerably higher than with bioassays. Samples sent to a laboratory will currently cost between $50.00 and $100.00 each, depending on which methods are used; and it could take several weeks or more to get back the results. Moreover, several samples per field must be assayed to determine overall residual herbicide levels and the cost, therefore, often becomes prohibitive. Therefore, less costly and more rapid alternatives for testing for trifluralin residues would be a welcome addition to these known test techniques.

Until recently, immunological techniques have been largely confined to medical and veterinary research, however, lately there have been some noteworthy successes in the field of horticulture, especially in the area of identification and control of various plant viruses. By way of background, the so-called "microplate enzyme linked immunosorbant assay" (ELISA) has had a significant impact on both the identification and control of several harmful plant pathogens. It is inexpensive, reliable and quite sensitive. Prior to the advent of this technique, while certain immunological methods were tried from time to time but, they proved to be of little value in agriculture, perhaps because of the cost and the high degree of technical expertise needed to carry them out. This is no longer true and the field of immunology holds great promise for agriculture. Unfortunately, realizing that immunological techniques are applicable does not solve the fundamental problem of designing and creating antigens which will evoke a desired immune response and result in the production of an antibody highly specific to any given chemical which is to be detected.

By way of further background in another area of immunology which relates to this invention, haptens are molecules that by themselves are too small, or for some other reason will not elicit an immune response. These smaller or non-immunogenic molecules must, therefore, be linked to a large protein before the resulting substance can elicit an immune response. Generally speaking, molecules with a molecular weight less than about 1,000 daltons need to be attached to a carrier protein in order to evoke such a reponse. Proteins with substances linked to their side-chains are referred to as "conjugated proteins". The side groups and the protein together make up the conjugated compound that will determine the antigenic response. It is essential that a functionality be present on the molecule of interest (the hapten) which will react with a protein. In addition, of course, it must assume a specifically to the targeted compound without responding to the presence of other analogous compounds. Despite the obvious difficulties associated with attempting to hypothesize the chemical make-up of an antigen that would produce a specific antibody, to say nothing of producing one having such a structure, we have succeeded in synthesizing an antibody which is highly specific to trifluralin.

U.S. Pat. No. 4,530,786 (the 786 patent), issued to the Applicants herein, is believed to be the closest prior art to the teachings of this patent application and the teachings of the 786 patent are specifically incorporated into this patent disclosure. The 786 patent teaches detection and quantification of small amounts of atrazine, i.e., 2-chloro-4-ethylamino-6-isopropylamino S-triazine:

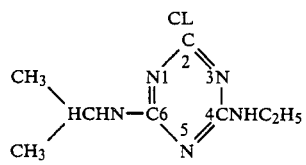

The detection and quantification of atrazine disclosed in the 786 patent was accomplished by first substituting a soluble, straight chain amino acid having at least four carbon atoms at the 4 or 6 position of the atrazine molecule so as to leave the chlorine exposed at the 2 position along with one of the remaining amino groups located at either the 4 or 6 position. The resulting substitution product acts as a hapten which is then conjugated at the site of the substituted amino acid group with a lysine-rich protein. This conjugated produce was used as an antigen to elicit an immune response which produces an antibody which is highly specific to atrazine.

However, as is well known in the art, and as is noted in the 786 patent, "realizing that immunological techniques are applicable does not solve the fundamental problem of designing and creating the antigen which will evoke the desired immune response and result in the production of an antibody specific to the molecule to be assayed". Theses words notwithstanding, Applicants, in attempting to design other antigens based upon some of the premises assumed in designing the antigen disclosed in the 786 patent, have discovered another antigen and other design premises which do not follow from those applicable to the atrazine specific antibody disclosed in the 786 patent, but which nonetheless have produced another very different, and distinctly useful, antibody. From the antigen design perspective, we postulated in the research which led to the 786 patent that the haptenic substitution product, like the atrazine, needed to have a chlorine atom exposed at the 2 position, and that the amino substituted atrazine molecule should be conjugated at either the amino ehtyl group in the 4 position or at the amino isopropyl group in the 6 position. We also postulated that the remaining amino group had to be left exposed for detection by the response mechanism. Moreover, the amino acid used in the 786 patent disclosure was postulated to require at least four carbon atoms.

These problems did not however remain valid with respect to the design of an entirely different antigen which we have found to be capable of eliciting the production of an antibody which is highly specific to trifluralin—a member of the dinitro analine family and a widely used herbicide. Trifluralin has the structural formula:

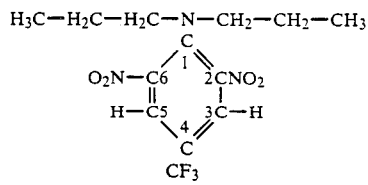

The structure of trifluralin as well as its known chemical reactivities are such that the chemical and biological reasoning used in designing the antigen disclosed in the 786 patent were not applicable. For example, trifluralin, unlike atrazine, has no chlorine in its 2 position; in fact trifluralin has no chlorine anywhere in its structure. Similarly, upon substitution of a soluble, straight chain amino acid to trifluralin, the resulting molecule, unlike atrazine, has no unreacted, exposed amino group anywhere in its structure. Nonetheless, the antigen disclosed herein is capable of evoking the production of another distinct antibody which is highly specific to trifluralin. Moreover, the trifluralin can undergo a reaction with a soluble, straight chain amino acid having as few as one carbon, as opposed to the four carbon atom lower limited established in the case of the atrazine substitution disclosed in the 786 patent.

Those skilled in the art will of course appreciate that once an antibody such as the one disclosed in this patent application has been produced, it can form the basis for a number of different assay procedures. For example, it could be used in microplate enzyme linked immunosorbant assay (ELISA) procedures. However, for reasons having to do with relative costs and the level of technical skills required, radioimmunoassay procedures are highly preferred for the practice of this invention. They are especially suited for detecting and quantifying the presence of trifluralin in such biologically important materials as plants, soil and water. Therefore, a little background information about radioimmunoassays also will serve to place our invention in further context with the prior art.

The basic principle of a radioimmunoassay is a competitive reaction of an antigen, such as the antigen disclosed in this patent application, as well as a radiolabeled form of that same antigen, for binding sites on an antibody which is highly monospecific to the antigen. Therefore a successful radioimmunoassay requires: (1) a specific, sensitive, high affinity antibody against the antigen that is to be measured; (2) a radioactivity labeled antigen of high specific activity that will react with the antibody with a comparable affinity to that of the unlabeled antigen; (3) availability of a suitable preparation of the antigen for use as a standard in the assay such that it will react with the antibody in a manner identical to that of the antigen in the sample being assayed; and (4) a simple, reproducible method of separating the antigen bound to the antibody from the free labeled antigen. A number of variations in the procedures used to carry out such assays are known to the art, see for example Freeman, Samuel and Gold, Phil, *Clinical Immunology*, 2nd Ed, 590–599, 1976. In all cases however, in order for a given radioimmunoassay test to be of use, it is essential that the given antigen/antibody dissociation reaction be specific for the anitgen to be measured.

However, nonspecific antibody production is often the rule rather than the exception. It often occurs in biological situations where structures of more than one substance are similar and/or where overlap, even in biological activities, may occur to some greater or lesser degree. By way of further background example, one such overlap situation is seen in the assay systems used to detect the glycoprotein pituitary hormones TSH, LH and FSH. Each of these hormones contains an identical alpha subunit. Biological activity, however, resides in the beta chains, which are slightly different in each of the three hormones. Hence, significant cross activity of these substances may occur with any given antibody. Moreover, injections of many substances during immunization procedures can result in formation of multiple antibodies that theoretically, and in fact, combine with any of several immunologically active sites on the antigen molecule. Other problems also exist. For example, it is also well known that antibody molecules of different specificities are often produced against any given hapten-protein complex. Consequently, finding antibodies with highly specific recognition capabilities, such as the one disclosed in this patent application, remains largely a difficult, empirical tasks.

Those skilled in the art will also appreciate that there are primarily two ways in which production of antibodies with sufficient affinity for use in radioimmunoassays have been achieved. For proteins and polypeptides of a molecular weight greater than about 5,000 daltons, the inherent immunogenicity of the substance itself usually results in production of sufficient antibody for development of an assay system. However, for biologically active compounds of lower molecular weights (haptens), especially those with molecular weights less than about 1000 daltons, such as the one disclosed in this invention, antibody production can usually only be achieved by conjugation of the low molecular weight haptenic material with a protein having significantly greater molecular weights. In other words, conjugation is essential for eliciting an immune responses to small substances that have no inherent immunogenicity and therefore cannot induce antibody formation. It is well known in the art that a variety of proteins can be used for conjugation of low-molecular-weight haptens such as the trifluralin based antigen disclosed in this patent application. Some of the more common protein materials used for this purpose include bovinve serum albumin, ovalbumin, thyroglobulin and fibrinogen. Here again however, such variations in these known conjugation procedures and materials do not in any way negate the need for antibody specificity in whatever assay procedure is ultimately employed.

SUMMARY OF THE INVENTION

Applicants' have discovered that an antibody highly specific to trifluralin can be produced by (1) substituting a soluble, straight chain amino acid for a propyl group of $\alpha,\alpha$, $\alpha$-trifluoro-2,6-dinitro-N-N dipropyl-p-toluidine, thereby leaving the trifluoro group at the 4 position, the nitro group at the 2 position and the other nitro group at the 6 position exposed (2) conjugating the resulting substituted compound at the site of the substituted soluble, straight chain amino acid with a lysine-rich protein to produce an antigen, and (3) inoculating an animal or suitable antibody-producing cell line, with the antigen and thereafter harvesting the antibody elicited in the host in response to the antigen. Those skilled in the art will appreciate that either an animal or an antibody producing cell line can be used as an antibody producing biological system in the practice of this invention. The animal system has certain advantages in the realm of research and small scale production while antibody producing cell lines are particularly well suited to large scale production of the antibody. A highly preferred hapten for conjugation is $\alpha$, $\alpha$, $\alpha$-trifluoro-2,6 dinitro-N-N-propyl, propionic acid-p-toluidine. This haptenic material is also characterized by having an exposed trifluoro group at the 4 position and 2 exposed nitro groups, one at the 2 and the other at the 6 position. This structure provides for highly specific detection by the animal's immunological mechanism or by a suitable antibody-producing cell line. The amino acid portion of the hapten replaces a propyl portion of the trifluralin and becomes the site for conjugation with the lysine-rich protein.

Various amino acids can be used to substitute a propyl group of the $\alpha$, $\alpha$, $\alpha$-trifluoro-2,6-dinitro-N-N dipropyl-p-toluidine. Soluble, straight chain amino acids having at least one carbon atoms are highly preferred. Larger amino acid molecules can be used up to the point at which they become so insoluble that they are ineffective for the purposes of this invention. Generally, this occurs after the amino acid molecule has about fourteen carbons. The lysine-rich protein used in the practice of this invention can be taken from any number of known sources, such as for example, rabbit serum albumin ("RSA"), human serum albumin, bovine serum albumin, ovalbumin, tyroglobulin and fibrinogen.

Whatever lysine-rich protein is used in the conjugation, the resulting conjugation product is then used as an antigen. As previously noted, it can then be introduced into a host biological system such as an antibody producing cell line or into laboratory animals, preferably by injection, to evoke an immune response to the host biological system. Preferred animals for this purpose would include rabbits, guinea pigs and dogs. The specificity of our particular antigen is evidenced by the fact that little or no detectable immune response is produced, even by very closely related compounds.

Our injection procedures, like many others of a similar nature, remain somewhat empirical but were largely based upon multiple injections of our antigen. Our antigen also can be associated with other substances such as, for example, Fruend's adjuvant. Additional injections are preferably given at intervals over 6 to 8 weeks. Peak antibody response usually occurs at about 90 days following the third or fourth injection. A sufficient number of animals must be injected to insure that at least some of the animals will produce good anitbody samples. In any case, the antibody produced from the hapten/lysine-rich protein conjugation can then be used to detect and quantify the presence of trifluralin in various substances, particularly in such biologically significant substances as plant materials, soils, and water. The immunoassays resulting from the use of the antibody produced by the antigen prepared by the above methods are capable of quantitatively detecting the presence of trifluralin in the low parts-per-billion (PPB) range. Moreover, the specificity of the assay is such that there is little or no detectable immune response in the presence of even closely related compounds.

Again, radioimmunoassay procedures, particularly those using isotopes of iodine are highly preferred in the quantification aspects of this invention. They generally involve substitution of iodine, produced by oxidation of iodide into ionized tyrosine residues of the protein carrier by use of oxidants such as chloramine T. Preferably $^{125}$I with its 60 day half-life is highly to $^{131}$I which has only a 8 day half-life. Iodinated thyrosine methyl esters are highly preferred for the radiolabeling function. Several percursors, metabolitis and degradation products of the targeted compound, show little or no reactivity in such assays. This fact can be verified using microplate enzyme linked immunoassay (ELISA) to corroborate the results of radiolabeling techinques.

DESCRIPTION OF THE PREFERRED EMBODIMENTS

The following examples illustrate preferred techniques for preparing and using the antigen and the antibody used in the practice of this invention. These examples are offered for purposes of illustration and should not be construed as limitations on the broader teachings of this invention.

Preparation of Hapten. β-propylaminopropionic acid (I) was prepared by mixing ethyl acrylate and propylamine in 1:10 molar amounts and stirring at room temperature for 4 hours then distilled (b.p. 74°/6 mm, n 20/D 1.4258, yield 80% of aminoester). The ester was hydrolyzed by stirring with cold water for 12 hours. The solution was roto-vaced to dryness and the solid residue recrystallized from ethanol and acetone. Yield of white crystalline acid 80% (m.p. 150°-151°).

3,5-dinitro-4-chlorobenzotrifluoride (II) was prepared by nitration of 4-chloro-benzotrifluoride with fuming nitric acid and fuming sulfuric acid at 100° for 3 hours. After work up and recrystallization from ethanol the material melted at 58°.

Then hapten α, α, α-trifluro-2,6-dinitro-N-N-propyl,-propionic acid-p-toluidine (III) was prepared by reacting I and II. To 270 mg (0.1 mM) 3,5-dinitro-4-chloro-benzotrifluoride (II) in 30 ml of dry chloroform was added 600 mg (0.450 mM) of -propylaminopropionic acid (I) and the solution stirred overnight at room temperature. To the reaction mixture was added 20 ml of N-HCl, stirred and transferred to a separatory funnel, the organic layer was washed well with water and roto-vaced to dryness. To the residue was added 10 ml 0.2N sodium hydroxide and the basic solution washed with ethyl acetate then acidified to pH 3 with 5% HCl. The deep yellow oily mixture was extracted with ethyl acetate (2×30 ml) and the extract washed with water dried and the solvent removed at reduced pressure to yield 300 mg (82%) of orange colored oil. Several attempts to solidify the product failed. Thin layer chromatography on Silica gel F254 developed with chloroform-methanol-water (24:7:1) and visualized with u.v. and chlorine reagent showed a single spot at Rt.68. NMR and IR consistent with desired compound.

Preparation of Antigen. For conjugation of the hapten material to protein, the mixed anhydride method was chosen because of the very slight solubility of the hapten in any but strongly basic aqueous solutions, whereas other methods at lower pH and aqueous solutions tend to precipitate the material from the protein solution before conjugation can occur. In any case, 36.5 mg (0.1 mM) of hapten was dissolved in 1.4 ml of dry DMF. To this was added 0.048 ml (0.2 mM) of tri-n-butylamine and the solution cooled to 0° to 5° in a stoppered tube. To the mixture was added 0.0133 ml (0.1 mM) of isobutyl chloroformate and the reaction allowed to proceed in an ice bath for 30 minutes. The resulting mixture was then added to a stirred ice cooled solution to 100 mg (0.00165 mM) of BSA, 1 ml water, 0.1 ml N sodium hydroxide and 2 ml DMF. Stirring in ice was continued and after 30 minutes 0.18 ml N NaOH was added and allowed to come to room temperature overnight, the pH remaining at 8 throughout the reaction. The produce was dialyzed against running water for 72 hours and brought to pH 4.5 with dilute hydrochloric acid. The resulting precipitate was allowed to stand in the cold for several hours, then separated by centrifugation and washed with cold acetone. This product was suspended in water and redeveloped by addition of 0.1 N NaOH to pH 7.8.

The resulting solution was dialyzed for 8 hours and lyophilized, yielding 100 mg. It is estimated tha 20 hapten units are conjugated to each protein molecule. The hapten also was then conjugated to RSA, ovalbumin and HSA by the same procedure.

Preparation of Hapten-Tyrosine Methyl Ester. Eighteen point two mg (0.5 mM) of hapten in 0.45 ml dry DMF was mixed with 0.0024 ml (0.1 mM) tri-n-butylamine and the solution cooled to 0° to 5°. This was followed by the addition of 0.007 ml (0.05 mM) isobutyl-chloroformate. The solution was allowed to react in the ice bath for 30 minutes and then was added to a cold solution of 10 mg (0.05 mM) tyrosine methyl ester hydrochloride in 3 ml 50—50 DMF-water and 0.065 ml N NaOH. Stirring in ice was continued and the solution was allowed to come to room temperature overnight, then diluted with 10 ml of water. The mixture was extracted into ethyl acetate, separated and washed twice with 10% HCL once with 10% sodium carbonate, then water and dried. The solvent was evaporated at reduced pressure and the solid residue purified by preparative TLC on a Silica Gel-60-F254-2 mm. The plate was developed with chloroform-methanol-water 25:7:1. It showed one major spot at Rt.41. This was scraped off and eluted with methanol to yield 24 mg of the desired compound.

Inoculation of Antigen. New Zealand white rabbits were inoculated with the conjugated hapten, boosted at predesignated intervals and bled once a week once a titer was established. Those skilled in the art will of course recognize that many animals suitable for production of antibodies can be used in place of the rabbits. Antibody producing cell lines capable of producing monoclonal antibodies also could be entirely satisfactory for production of this antibody.

The titer was measured by both radioimmunoassay (RIA) using the TME conjugate and by enzyme linked immunosorbant assay (ELISA) using the OA-conjugated hapten. Both methods showed a high degree of recognition to trifluralin after about 8 weeks and 4 boosts. It was found that trifluralin could be attached directly to the polystyrene ELISA plates thereby eliminating the need for the OA-conjugated hapten. Several precursors, metabolites and dagradation products of trifluralin were checked for cross reactivity. If any cross reactivity was found the serum was cleaned up on a CNB activated superose 4B column using the compound that was causing background problems. Soil samples containing known quantities of trifluralin were extracted by various methods and checked by ELISA.

Again, once the antigen is produced it is not only necessary to analyze for specificity but, in addition, to develop techniques to utilize this specificity in a practical manner. As noted above, several forms of assay could have been used. We employed a radioimmunoassay in a competitive binding test using a radio-iodinated thyrosine methyl ester. Our tests proved to be extremely sensitive, down to the nanogram level ($1 \times 10^{-9}$ g). However, such tests require special licensing to use the radioactive material involved. A farm would not need the kind of precision that can be obtained by a radioimmunoassay, but once this methodology is mastered it would be less expensive to run multiple tests in comparison with other laboratory methods that assay to the same degree of accuracy.

Enzyme linked immunosorbant assay appears to have the greatest promise in the field, or at least at the less well equipped laboratory. A minimum of equipment is required to perform the procedure and, once the techniques are perfected, they require no skilled technical personnel or special safety procedures to complete. The basis for the assay is a polystyrene well which will bind unselectively many organic substances. Various layers are placed in the well "sandwich" fashion until a color fraction indicates the amount of trifluralin present. An inexpensive optical reader can then be used to measure the amount of trifluralin present in the sample at a very modest expense. Those skilled in the art will of course appreciate that many further examples could be given without departing from the scope and spirit of the broader teachings of this invention.

Thus having disclosed our invention we claim:

1. An antibody for an immunoassay for trifluralin, said antibody made by a process comprising:
   substituting a soluble, straight chain amino acid having at least one carbon atom for a propyl group of α, α, α-trifluoro-2-6-dinitro-N-N-dipropyl-p-tuluidine such that the trifluouro group at the 4 position, the nitro group at the 2 position and the other nitro group at the 6 position are left exposed to produce a resulting substitution product;
   conjugating the resulting substitution product, at the site of the amino acid, with a lysine-rich protein to produce an antigen;
   inoculating a host antibody producing biological system with the antigen to elicit production of an antibody specific to trifluralin; and
   harvesting the antibody specific to trifluralin form the host antibody producing biological system.

2. The antibody of claim 1 wherein the conjugation of the resulting substitution product with a lysine-rich protein is carried out using a mixed anhydride method.

3. The antibody of claim 1 wherein the soluble, straight chain amino acid has between one and about fourteen carbon atoms.

4. The antibody of claim 1 wherein the lysine-rich protein is selected from the group consisting of bovine serum albumin, ovalbumin, rabbit albumin, human serum albumin, thyroglobulin and fibrinogen.

5. An antibody for an immunoassay for trifluralin, said antibody made by process comprising:
   substituting a soluble, straight chain amino acid having at least one carbon atom for a propyl group of 3,5-dinitro-4(β-propylaminopropionic acid)—benzotrifluoride such that the trifluoro group at the 4 position, the nitro group at the 2 position and the other nitro group at the 6 position are left exposed to produce a resulting substitution product;
   conjugating the resulting substitution product, at the site of the amino acid, with a lysine-rich protein to produce an antigen;
   inoculating a host antibody producing biological system with the antigen to elicit production of an antibody specific to trifluralin; and
   harvesting the antibody specific to trifluralin from the host antibody producing biological system.

6. The antibody of claim 5 wherein the conjugation of the resulting substitution product with a lysine-rich protein is carried out using a mixed anyhdride method.

7. The antibody of claim 5 wherein the soluble, straight chain amino acid has between one and about fourteen carbon atoms.

8. The antibody of claim 5 wherein the lysine-rich protein is selected from the group consisting of bovine serum albumin, ovalbumin, rabbit serum albumin, human serum albumin, thyroglobulin and fibrinogen.

9. In an immunoassay for the detection of trifluralin comprising:
   a. providing a sample suspected of containing trifluralin;
   b. contacting an antibody with the sample;
   c. detecting the presence of a reaction between the antibody and said sample wherein the presence of a reation is an indication of the presence of trifluralin and no reaction indicates no trifluralin is present wherein the improvement comprises employing the antibody of claim 1.

10. The method of claim 9 wherein the conjugation of the substitution product, at the site of the amino acid, is carried out using a mixed anhydride method; the soluble, straight chain amino acid has between one and about fourteen carbon atoms; the lysine-rich protein is selected from the group consisting of bovine serum albumin, ovalbumin, rabbit serum albumin, human serum albumin, thyroglobulin and fibrinogen and the immunoassay is based upon the ability of the antibody to selectively bind with trifluralin.

11. In an immunoassay for the detection of trifluralin comprising:
   a. providing a sample suspected of containing trifluralin;
   b. contacting an antibody with the sample;
   c. detecting the presence of a reaction between the antibody and said sample wherein the presence of a reaction is an indication of the presence of trifluralin and no reaction indicates no trifluralin is present wherein the improvement comprises employing the antibody of claim 5.

12. The method of claim 11 wherein the conjugation of the substitution product, at the site of the amino acid, is carried out using a mixed anhydride method; the soluble, straight chain amino acid has between two and about fourteen carbon atoms; the lysine-rich protein is selected from the group consisting of bovine serum albumin, ovalbumin, rabbit serum albumin, human serum olbumin, thyroglobulin and fibrinogen and the immunoassay is based upon the ability of the anitbody to selectively bind with trifluralin.

* * * * *